United States Patent

Schlosser et al.

[11] Patent Number: 5,872,301
[45] Date of Patent: Feb. 16, 1999

[54] BIFUNCTIONAL PRECURSORS FOR THE PREPARATION OF LIQUID CRYSTALS

[75] Inventors: Hubert Schlosser, Glashütten; Rainer Wingen, Hattersheim; Javier Manero, Frankfurt, all of Germany

[73] Assignee: Hoechst Aktiengesellschaft, Frankfurt, Germany

[21] Appl. No.: 428,102

[22] PCT Filed: Oct. 6, 1993

[86] PCT No.: PCT/EP93/02732

§ 371 Date: Jun. 13, 1995

§ 102(e) Date: Jun. 13, 1995

[87] PCT Pub. No.: WO94/10152

PCT Pub. Date: May 11, 1994

[30] Foreign Application Priority Data

Oct. 26, 1992 [DE] Germany .......................... 42 36 104.4

[51] Int. Cl.$^6$ .......................... C07C 41/00; C07C 39/00; C09K 19/34; C09K 19/32
[52] U.S. Cl. .............. 568/647; 252/299.61; 252/299.62; 252/299.66; 568/716
[58] Field of Search .......................... 252/299.66, 299.61, 252/266.62; 568/647, 716

[56] References Cited

U.S. PATENT DOCUMENTS

| | | | |
|---|---|---|---|
| 4,835,274 | 5/1989 | Kano . | |
| 5,389,291 | 2/1995 | Reiffenrath et al. | 252/299.61 |
| 5,441,668 | 8/1995 | Hornung et al. | 252/299.01 |
| 5,447,656 | 9/1995 | Jungbauer et al. | 252/299.01 |
| 5,460,749 | 10/1995 | Terada et al. | 252/299.61 |
| 5,462,694 | 10/1995 | Kosaka et al. | 252/299.61 |

FOREIGN PATENT DOCUMENTS

| | | |
|---|---|---|
| PA 0 225 195 A1 | 6/1987 | European Pat. Off. . |
| PA 0 284 093 A1 | 9/1988 | European Pat. Off. . |
| PA 0 313 284 A2 | 4/1989 | European Pat. Off. . |
| PA 0 313 338 A2 | 4/1989 | European Pat. Off. . |
| PA 0 339 252 A2 | 11/1989 | European Pat. Off. . |
| PA 0 354 434 A2 | 2/1990 | European Pat. Off. . |
| PA 0 360 042 A1 | 3/1990 | European Pat. Off. . |
| PA 0 360 622 A2 | 3/1990 | European Pat. Off. . |
| PA 0 394 906 A2 | 10/1990 | European Pat. Off. . |
| PA 0 439 089 A1 | 7/1991 | European Pat. Off. . |
| PA 0 517 498 A1 | 12/1992 | European Pat. Off. . |
| 42 20 065 A1 | 12/1993 | Germany . |
| 56-118798 | 9/1981 | Japan . |
| 59-92099 | 5/1984 | Japan . |
| 62-49918 | 3/1987 | Japan . |
| 62-289300 | 12/1987 | Japan . |
| 278499 | 3/1990 | Japan . |
| 2 197 868 | 6/1988 | United Kingdom . |
| WO 89/06678 | 7/1989 | WIPO . |
| WO 91/05029 | 4/1991 | WIPO . |

*Primary Examiner*—C. H. Kelly
*Attorney, Agent, or Firm*—Frommer Lawrence & Haug LLP

[57] ABSTRACT

Bifunctional compounds of the formula (I), $$\text{Hal}-\left[\langle D \rangle\right]_l-\langle E \rangle-\langle F \rangle-\text{OCH}_2-\langle \text{Ar}(R^3)_n \rangle \quad (I)$$

in which:

$-\langle D \rangle-$ and $-\langle E \rangle-$ are naphthalene-2,6-diyl or $$-\left\langle \begin{array}{c} X-U \\ \bigcirc \\ Y-Z \end{array} \right\rangle-$$

$-\langle F \rangle-$ is naphthalene-2,6-diyl or $$-\left\langle \begin{array}{c} (F)_m \\ \bigcirc \end{array} \right\rangle-$$

U, X, Y and Z are —CH=, —CF= and —N=, with the proviso that —CF= and —N= may each only be represented at most twice per six-membered ring, and that —CF= and —N= may not at the same time be represented twice in a six-membered ring;
Hal is Cl, Br or I; or H, if X and/or Y are —CF=
$R^3$ is $CH_3$ or $OCH_3$
l is 0 or 1
m and n are 0, 1, 2 or 3.

The compounds of the formula I are useful intermediates for the preparation of liquid-crystalline mixtures.

8 Claims, No Drawings

BIFUNCTIONAL PRECURSORS FOR THE PREPARATION OF LIQUID CRYSTALS

BACKGROUND OF THE INVENTION

The unusual combination of anisotropic and fluid behavior of liquid crystals has resulted in their use in electro-optical switching and display devices, where their electrical, magnetic, elastic and/or thermal properties can be utilized to cause changes in alignment. Optical effects can be achieved, for example, with the aid of biorefringence, the inclusion of dichroically absorbing dyes ("guest-host mode") or light scattering.

In order to satisfy the constantly increasing practical requirements in the various areas of application, there is a constant demand for new improved liquid-crystal mixtures and thus also for a large number of mesogenic compounds of various structures. This applies both to applications in which nematic liquid-crystal phases are used, and to those having smectic liquid-crystal phases.

The processes for the preparation of the components of such liquid-crystal mixtures also have to meet constantly increasing requirements, in particular with respect to the effects on ecology, but also with respect to process economy. The liquid-crystal mixtures virtually always comprise at least two different classes of substance, and very frequently at least two homologs differing, for example, in the chain length of an alkyl or alkoxy substituent are very frequently found in a certain class of substances (see, for example, EP-A 497 176, U.S. Pat. No. 5,026,506, EP-A 495 686, EP-A 319 167, EP-B 317 587, EP-A 316 181, EP-A-315 958).

Attempts have therefore already been made to find ways in which the syntheses of various classes of substance, but ones which contain common part-structures, can be accomplished on the basis of the same precursors.

EP-A 354 434 describes derivatives of boric acid, including boronic acids, which are reacted with certain halogen compounds with catalysis with metal compounds to give liquid-crystal compounds.

However, a significant disadvantage of the compounds described in EP-A 354 434, which impairs inexpensive production and is ecologically unacceptable due to additional processing steps, is the fact that on further conversion into liquid-crystal compounds for the preparation of more than one homolog of a substance class, in each case more than one boric acid derivative or halogen compound is necessary, since the substitution pattern of the desired target molecules is already defined in the starting compounds for the boric acid derivatives or hydrogen compounds, and homologization is no longer possible in the subsequent reaction steps.

For the preparation of different classes of substance—which is taken to mean here, for example, not only phenylpyridine versus phenylpyrimidine, but also, for example, 5-alkyl- versus 5-alkoxy- versus 5-alkoxycarbonyl- versus 5-alkylcarbonyloxypyrimidine, since significant differences with respect to mesogenic properties, stability, synthesis and thus not least also of the precursors exist—different precursors must in each case be prepared in accordance with the prior art.

DETAILED DESCRIPTION OF THE INVENTION

The disadvantages described are overcome by the novel bifunctional compounds of the formula (I), $$Hal-\left[\langle D\rangle\right]_l-\langle E\rangle-\langle F\rangle-OCH_2-\langle\bigcirc\rangle-(R^3)_n \quad (I)$$

in which:

$$-\langle D\rangle- \text{ and } -\langle E\rangle-$$

are naphthalene-2,6-diyl or $$-\langle\overset{X-U}{\underset{Y-Z}{\bigcirc}}\rangle-$$

$$-\langle F\rangle-$$

is naphthalene-2,6-diyl or $$-\langle\overset{(F)_m}{\bigcirc}\rangle-$$

U, X, Y and Z are —CH═, —CF═ and —N═, with the proviso that —CF═ and —N═ may each only be represented at most twice per six-membered ring, and that —CF═ and —N═ may not at the same time be represented twice in a six-membered ring;

Hal is Cl, Br or I; or H, if X and/or Y are —CF═

$R^3$ is $CH_3$ or $OCH_3$ l is 0 or 1 m and n are 0, 1, 2 or 3.

Preference is given to compounds in which l=0 at least one of U, X, Y and Z is —N═ and at most one is —CF═, and the others are —CH═ m is 0, 1 or 2 n is 0, 1 or 2

$R^3$ is $CH_3$ or $OCH_3$

Hal is Br or I.

Particular preference is given to compounds in which l=0 one or two of U, X, Y and Z is —N═, and the others are —CH═ m is 0, 1, 2 or 3 n is 0

Hal is Br or I.

Very particular preference is given to compounds in which l=0 one or two of U, X, Y and Z is —N═, and the others are —CH═ m and n are 0

Hal is Br.

Particular preference is given to the compounds 1a–c.

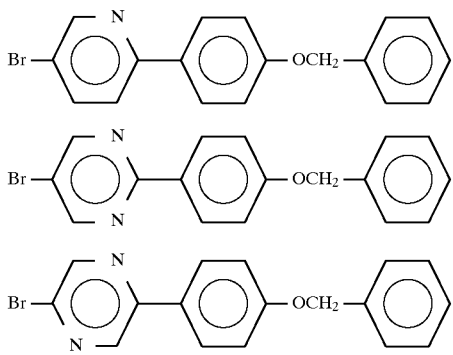

The novel compounds can be successively and selectively derivatized via their two different functionalities—the halogen and benzyl ether functions.

Thus, they can be reacted via the halogen function by metal-catalyzed processes, as described, for example, in DE-C 3 930 663 and EP-A 354 434, with boronic acids of Formula II

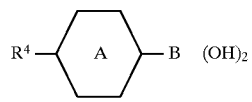

in which $R^4$=H, alkyl having 1 to 18 carbon atoms, in which, in addition, one or more nonadjacent —$CH_2$-groups can be replaced by —O—, —C(O)—, —CH=CH—, —OC(O)— and —Si($CH_3$)$_2$—, and

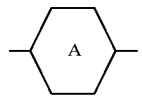

is 1,4-phenylene, optionally substituted once, twice or three times by F, to give intermediates of the formula (III)

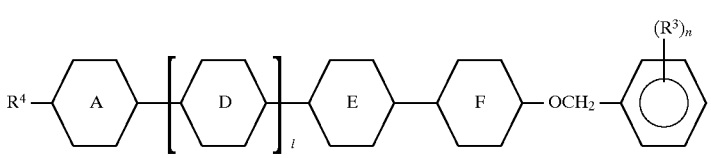

in which the symbols are as defined in (I) and (II).

Preference is given to the conversion, for example into compounds of the formula (III), by a process proposed in the German Patent Application P 42 36 103.6 with the title "Process for cross-coupling aromatic boronic acids with aromatic halogen compounds or perfluoroalkylsulfonates", in which the novel compound is coupled to aromatic halogen compounds or perfluoroalkylsulfonates in the presence of a base and catalytic amounts of metallic palladium, optionally on a support material, which comprises adding a base and catalytic amounts of a ligand to the reaction mixture.

It is furthermore possible to react the novel compounds of the formula I by metal-catalyzed processes, as described, for example, in DE-C 3 930 663 and EP-A 354 434, with alkyl organometallic compounds to give intermediates of the formula (IV)

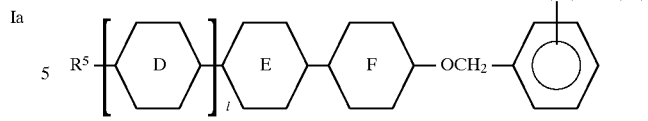

in which
$R^5$ is alkyl having 1 to 18 carbon atoms, in which, in addition, one or more non-adjacent —$CH_2$— groups can be replaced by —O—, —CH=CH— or —Si($CH_3$)$_2$—, where —O— must not be bonded directly to the ring,
and the other symbols are as defined in the formula (I).

In addition, it is possible to convert the halogen functions in the compounds of the formula (I) into an OH group by reaction with OH nucleophiles.

Novel compounds of the formula V

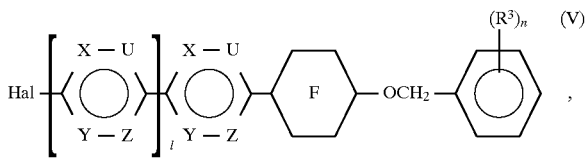

in which
the symbols are as defined in the formula (I), with the proviso that in

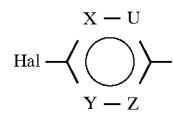

at least U and/or Z are —N= and X and/or Y must not be —N=,
are preferably reacted by a process proposed in the German Patent Application P 42 36 102.8 with the title, "Process for the preparation of hydroxyheteroaromatic compounds", with a metal hydroxide in a solvent under atmospheric pressure using catalytic amounts of sulphur to give com-

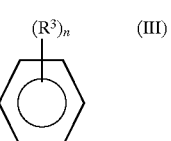

pounds of the formula VI

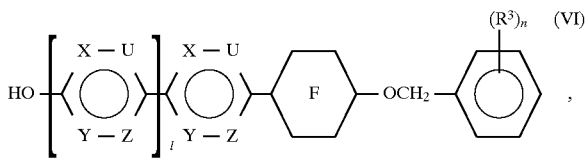

in which the symbols are as defined in formula (V).

These intermediates (VI) can be converted by standard methods of synthesis for alkyl aryl ethers or aryl alkanoates, into intermediates of the formula (VII)

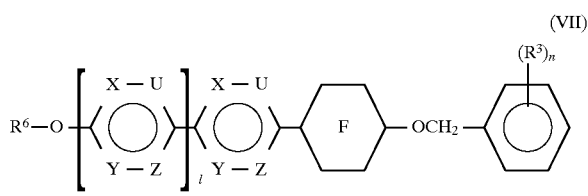
(VII)

in which
R$^6$ is alkyl having 1 to 18 carbon atoms, in which, in addition, one or more non-adjacent —CH$_2$— groups can be replaced by —O—, —C(=O)—, —CH=CH— or —Si(CH$_3$)$_2$—,
and the other symbols are as defined in the formula (V).

Furthermore, intermediates of the formula (VI) can be converted, by standard methods by reaction with carboxylic acids or carboxylic acid derivatives (for example halides or anhydrides), into intermediates of the formula (VIII)

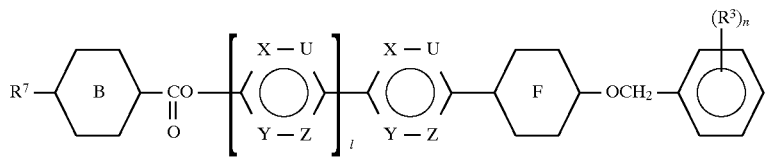
(VIII)

in which
R$^7$ is alkyl having 1 to 18 carbon atoms, in which, in addition, one or more non-adjacent —CH$_2$— groups can be replaced by —O—, —CH=CH— or —Si(CH$_3$)$_2$—,

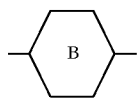

is 1,4-phenylene, optionally substituted once, twice or three times by F, or 1,4-cyclohexylene or 1,3-dioxane-2,5-diyl.

The intermediates (III), (IV), (VI), (VII) and (VIII) are likewise the subject-matter of the present invention.

Removal of the benzyl ether function in the intermediates (I), (III), (IV), (VII) and (VIII) by standard methods (for example described in T. W. Greene, P. G. W. Wuts, Protective Groups in Organic Synthesis, J. Wiley & Sons, New York, 1991, pp. 156–160) gives novel intermediates containing a phenolic OH function, which are likewise the subject-matter of the present invention:

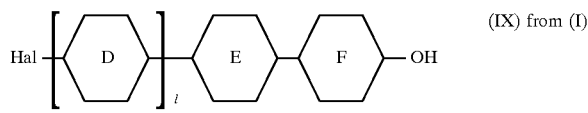
(IX) from (I)

(X) from (IV)

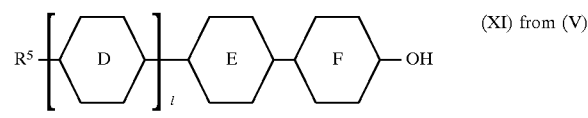
(XI) from (V)

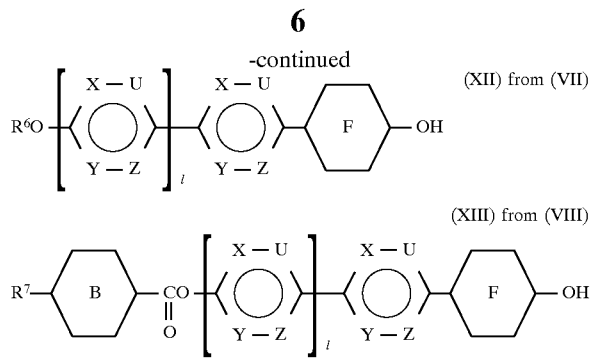
(XII) from (VII)

(XIII) from (VIII)

These phenolic compounds of the formulae (IX) to (XIII) can be converted, by standard methods, into numerous types of components for liquid-crystal mixtures. For example, reaction with alkyl halides or equiavlent alkylating agents gives aryl alkyl ethers of the formula (XIV)

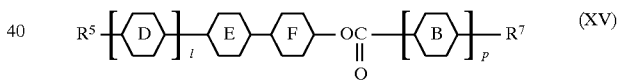
(XIV)

in which the symbols are as defined in the formula (III).
Analogous reactions can be carried out with (XI), (XII) and (XIII).

Furthermore, reaction with carboxylic acids or carboxylic acid derivatives (for example halides or anhydrides) gives aryl carboxylates, for example (XV) from (XI)

$$R^5\text{—}[\langle D\rangle]_l\text{—}\langle E\rangle\text{—}\langle F\rangle\text{—OC(=O)—}[\langle B\rangle]_p\text{—}R^7 \quad (XV)$$

in which the symbols are as defined in the formulae (I) and (VIII), and p can be zero or one or two. Analogous reactions can be carried out with (X), (XII) and (XIII).

Furthermore, reaction of perfluoroalkanesulfonic acid derivatives with (IX), (X), (XI), (XII) or (XIII) gives perfluoroalkanesulfonic acid ester intermediates, which are coupled with boronic acids with metal catalysis by standard methods, as described, for example, in DE-C 3 930 663, EP-A 354 434 and German Patent Application P 42 36 103.6 with the title "Process for the cross-coupling of aromatic boronic acids with aromatic halogen compounds or perfluoroalkylsulfonates", to give components of liquid crystals of the formulae (XVI to XIX):

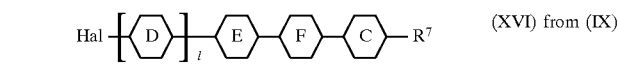
(XVI) from (IX)

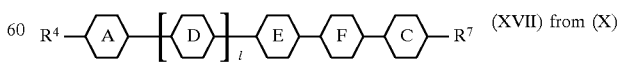
(XVII) from (X)

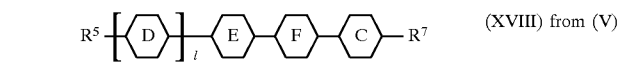
(XVIII) from (V)

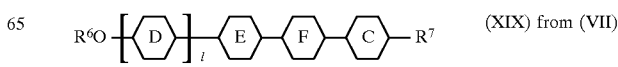
(XIX) from (VII)

in which
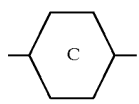
is 1,4-phenylene, which may also carry 1, 2 or 3 F substituents, or is pyridine-2,5-diyl or naphthalene-2,6-diyl.
Novel compounds of the formula (I) can preferably be used in one of the ways described above for the preparation of components of liquid crystals of the formula (XX)
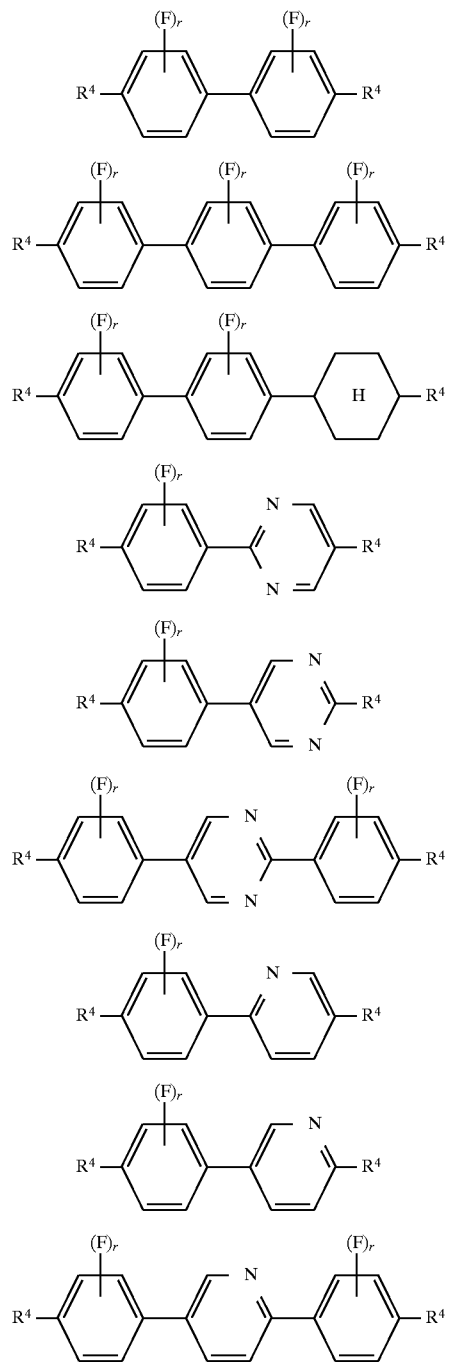
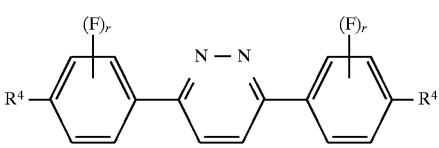
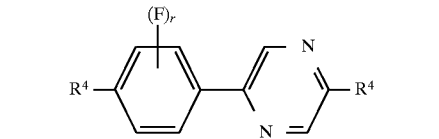
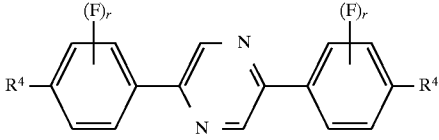
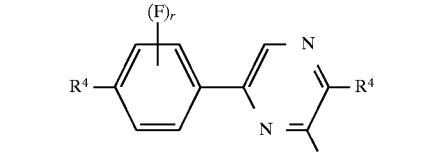
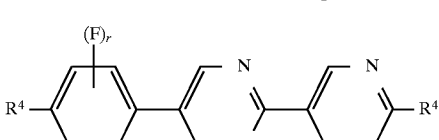
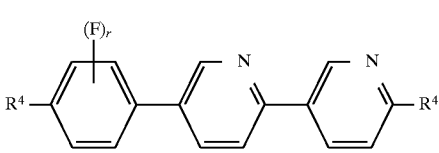
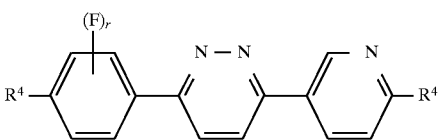
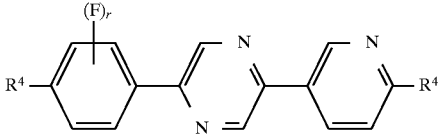
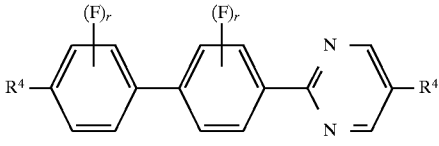

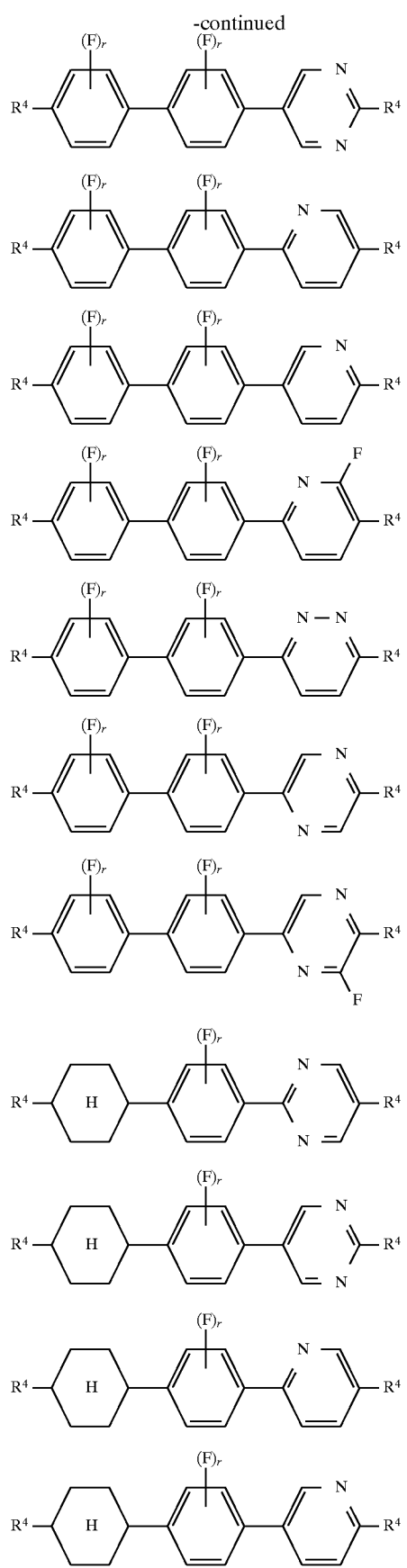

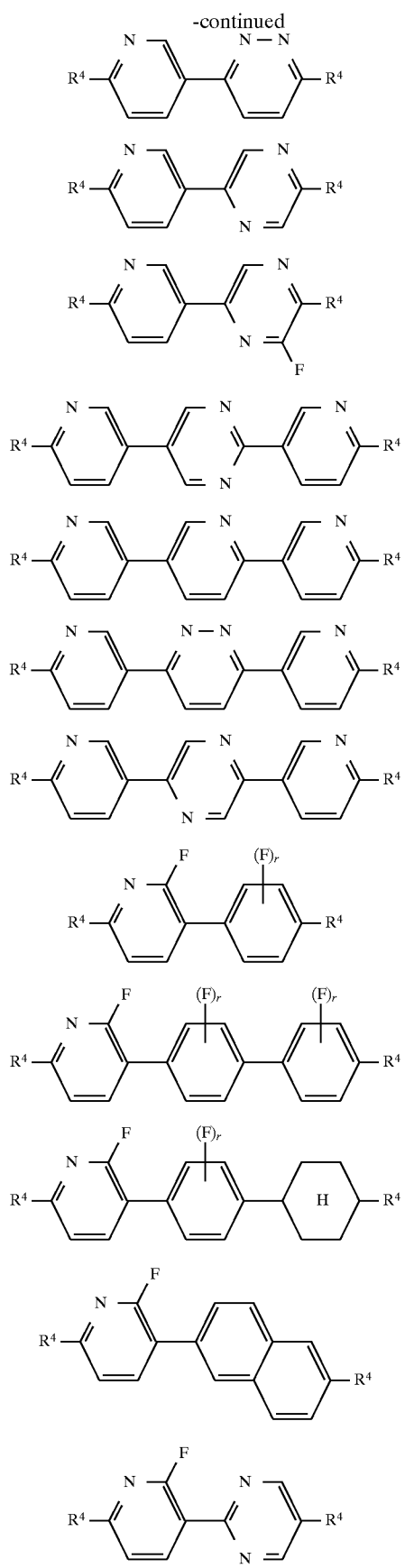
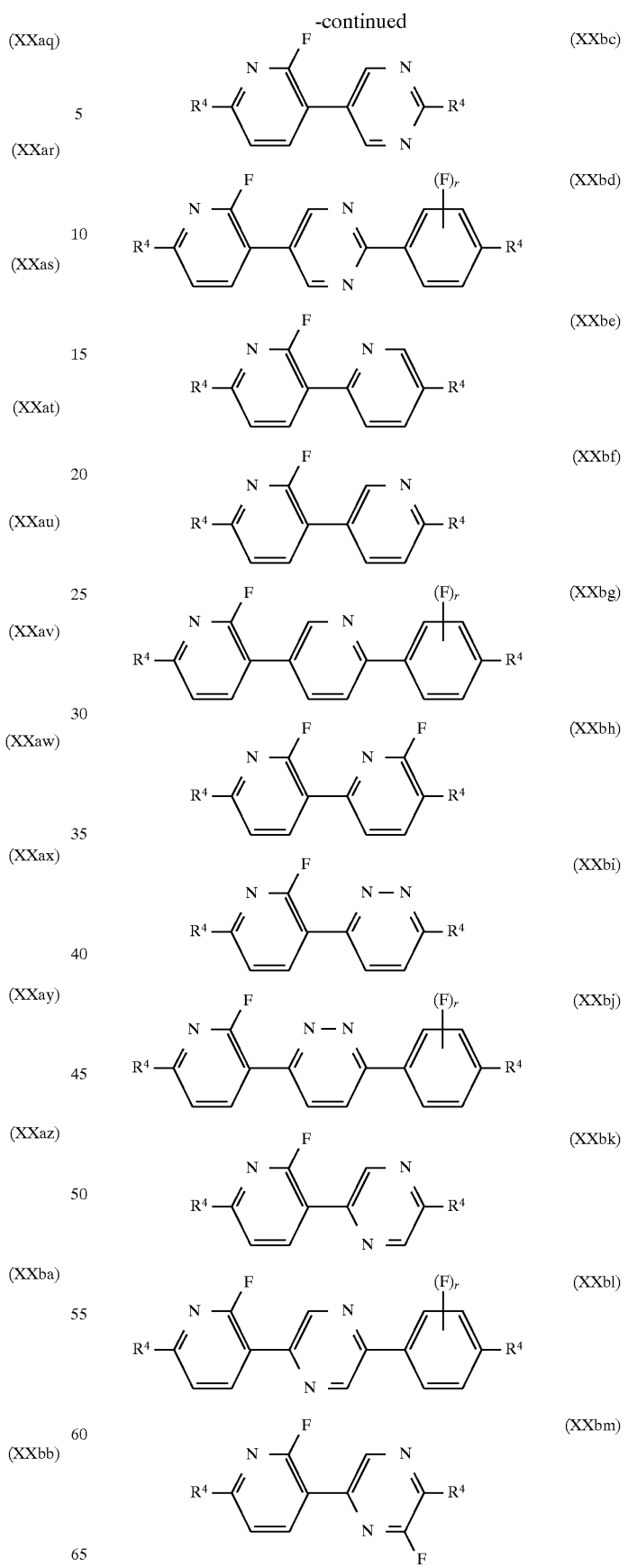

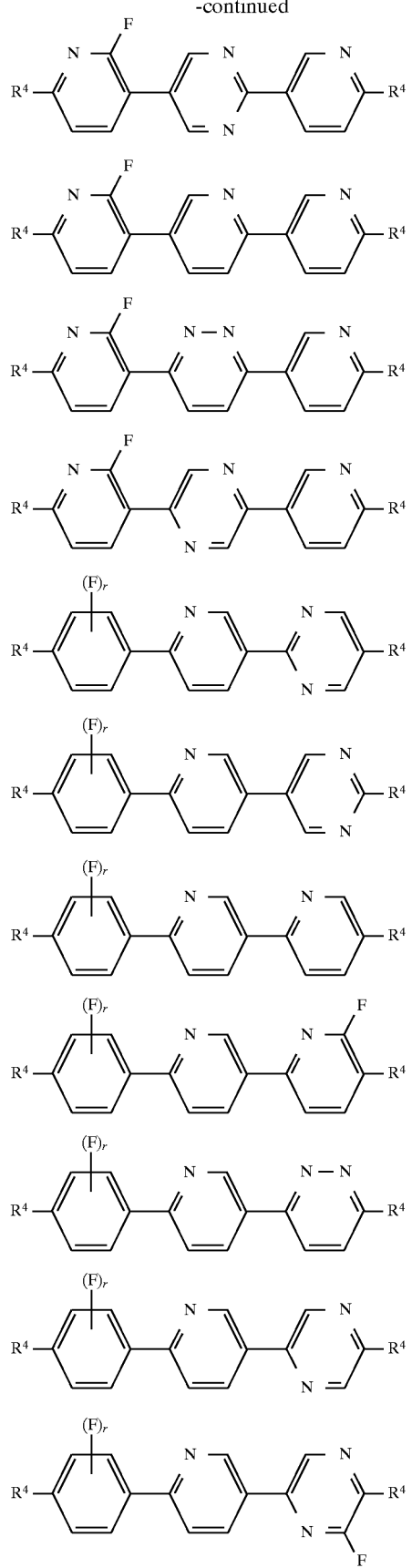

-continued

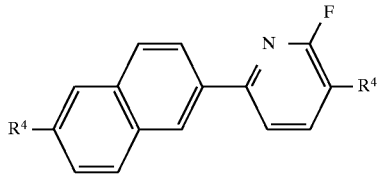 (XXcl)

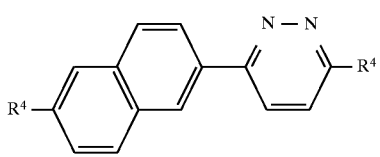 (XXcm)

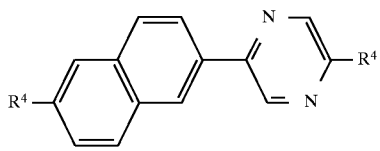 (XXcn)

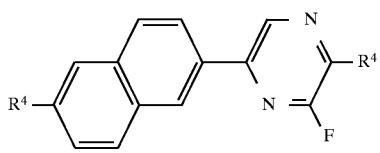 (XXco)

in which
r is 0, 1, 2 or 3, and
$r^4$ is as defined in the formula (II).

The compounds (I) can particularly advantageously be prepared by coupling an arylboronic acid of formula (XXI), as proposed in German Patent Application P 42 36 105.2 with the title "Arylboronic acids as precursors for the preparation of components of liquid crystals":

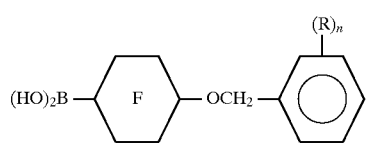 (XXI)

in which the substituents and indices have the following meanings:

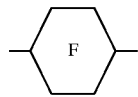

is naphthalene-2,6-diyl or

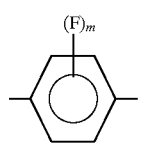

R is $CH_3$ or $OCH_3$
m is 0, 1, 2 or 3
n is 0, 1 or 2 by known processes (for example EP-A 354 434 or as proposed in German Patent Application P 42 36 103.6 with the title "Process for the cross-coupling of aromatic-boronic acids with aromatic halides or perfluoroalkylsulfonates"), with a halide of the formula (XXII):

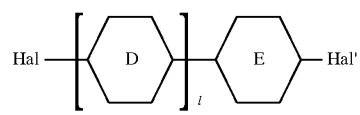 (XXII)

in which the symbols are as defined in the formula (I), and

Hal' is Cl, Br, I or perfluoroalkanesulfonate.

Preference is given to

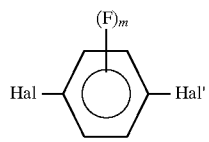 (XXIIa)

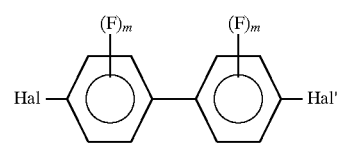 (XXIIb)

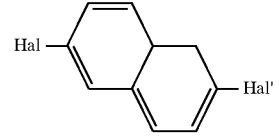 (XXIIc)

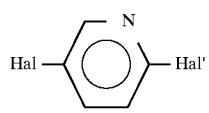 (XXIId)

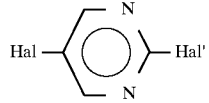 (XXIIe)

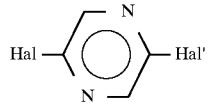 (XXIIf)

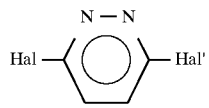 (XXIIg)

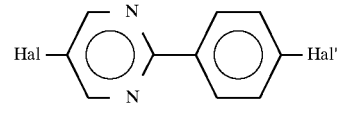 (XXIIh)

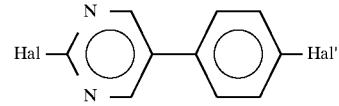 (XXIIi)

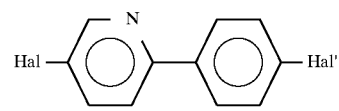 (XXIIj)

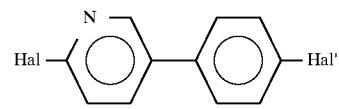 (XXIIk)

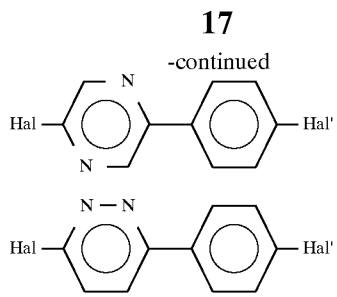

They are either commercially available, for example (XXIIa; m=0), (XXIId), (XXIIg) or can be obtained by standard methods from known or commercially available materials: for example (XXIIb, m=0) by reacting commercial 4-bromo-4'-hydroxybiphenyl with perfluroalkanesulfonic acid derivatives; for example (XXIIc) by reacting commercial 6-bromo-2-hydroxynaphthalene with perfluoroalkanesulfonic acid derivatives; (XXIIe) as described in J. Chem. Soc. (C) 1971, 1889, (XXIIm) analogously to Z. Chem. 17, 333 (1977); (XXIII) by reacting 2-(4-halophenyl)-5-hydroxypyrazine—prepared analogously to H. Heberer, Degree Thesis Halle, 1967, cited in "Flüssige Kristalle in Tabellen" [Liquid crystals in tables], ed. D. Demus, VEB Verlag für Grundstoffindustrie, Leipzig 1974, p. 265—with, for example, phosphorus halides or perfluoroalkanesulfonic acid derivatives; (XXIIk) analogously to (XXIII), but using 5-(4-halophenyl)-2-hydroxypyridine, prepared analogously to Z. Chem. 18, 403 (1978); (XXIIi) analogously to (XXIII), but using 5-(4-halophenyl)-2-hydroxypyrimidine, prepared analogously to J. Prakt. Chem. 501, 169 (1979); (XXIIh) analogously to Mol. Cryst. Liq. Cryst. 42, 1225 (1977); (XXIIf) as described in J. Am. Chem. Soc. 71, 2798 (1949); (XXIIj) analogously to "Adv. in Liquid Crystal Research and Application" (ed. L. Bata), Oxford, Pergamon Press, Budapest.

The novel compounds are versatile units for the synthesis of polycyclic aromatic compounds which can be employed in many areas of organic chemistry, for example for the preparation of components for the liquid-crystal mixtures, pharmaceuticals, cosmetics or crop-protection agents.

They are preferably used as intermediates for the preparation of components for liquid-crystal mixtures, in particular ferroelectric mixtures. Such components are described, for example, in EP-A 354 434, EP-A 307 880, EP-B 283 506, EP-B 357 702 and EP-A 439.089.

Use of the novel compounds of the formula (I) allows synthetic steps to be saved in the preparation of components for liquid-crystal mixtures, which brings enormous advantages, in particular, in large-scale industrial synthesis. The invention allows the provision of a broad product range from a single intermediate, which greatly simplifies the process from a technical, economic and ecological point of view.

A comparison of schemes 1A—for a process using compounds as per EP-A 354 434—and 1B—for a process using the novel compounds—shows that a total of 8 synthetic steps are necessary for the synthesis of 2 homologous phenylpyrimidines by the process using the compounds of EP 354 434, but only 7 synthetic steps are required for the preparation of the same two homologs in a process using the novel compounds of the formula (I).

The advantage is even clearer for process economy and ecology if—as described, for example in EP-A 307 880, Example 34—3 homologs or—as, for example, in EP-B 283 506, Example 5—4 homologs of a substance class are to be prepared.

Scheme 2A shows a synthesis using the compounds proposed in EP-A 354 434. For the preparation of the three homologous phenyl pyrimidines, 12 synthetic steps are required if said precursors are used. Scheme 2B shows the synthesis of the same 3 homologs, but using the novel bifunctional precursor (Ib); only 8 synthetic steps are necessary.

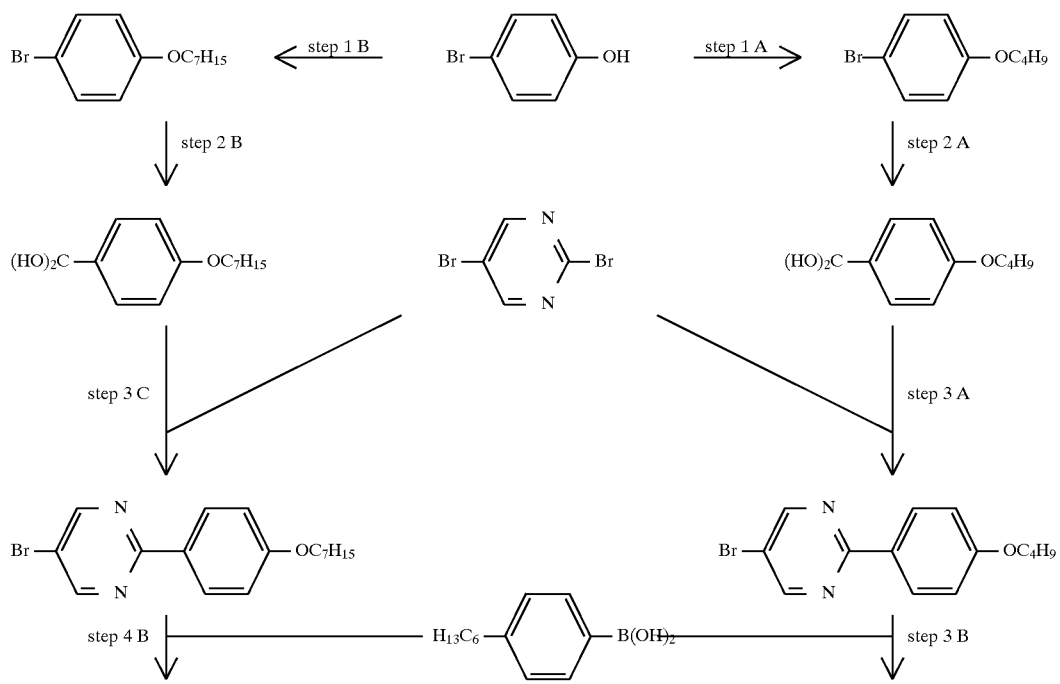

Scheme 1A

8 Synthetic steps

-continued
Scheme 1A
Scheme 1B
7 Synthetic steps
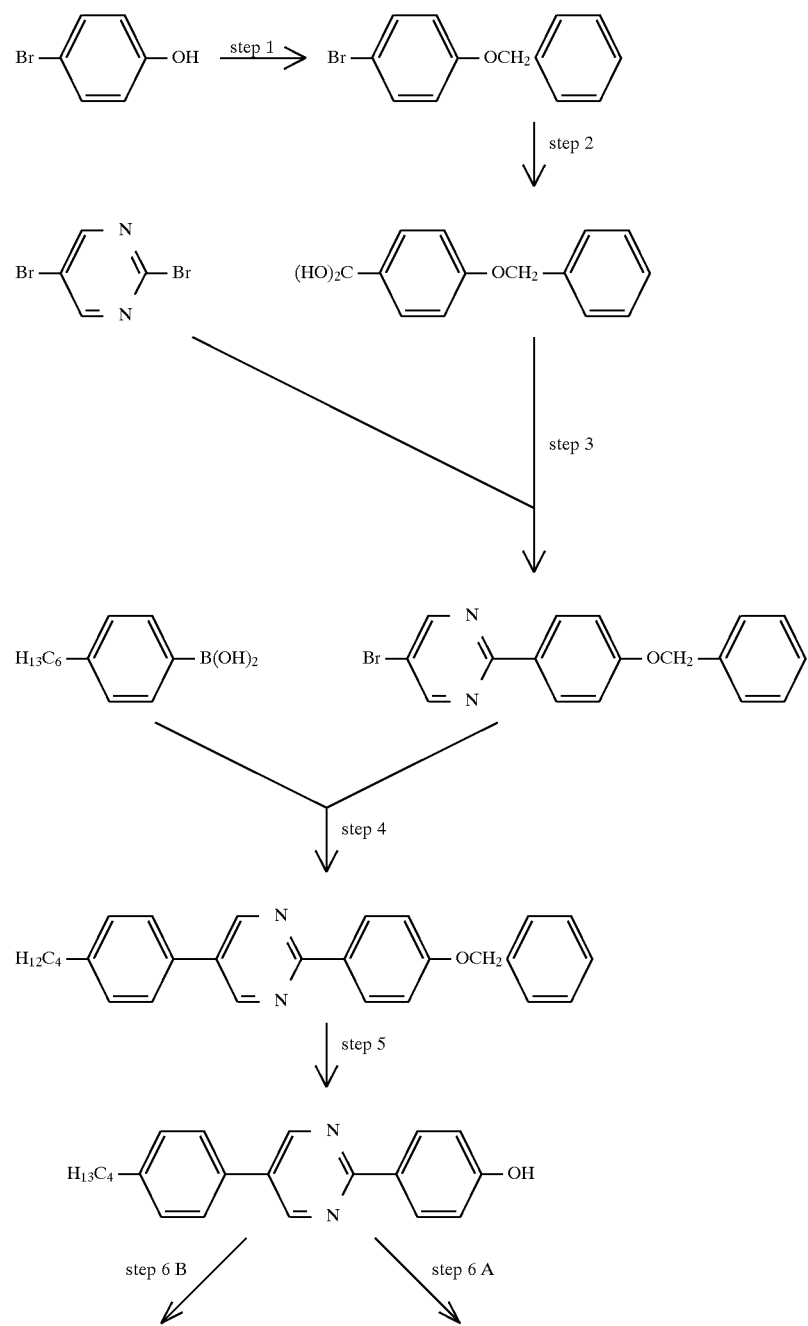

-continued
Scheme 1B
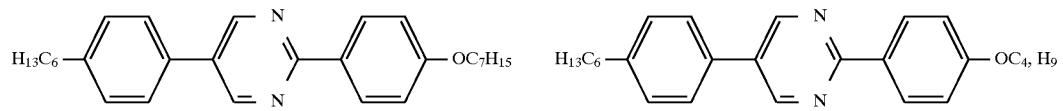
Scheme 2A
12 Synthetic steps
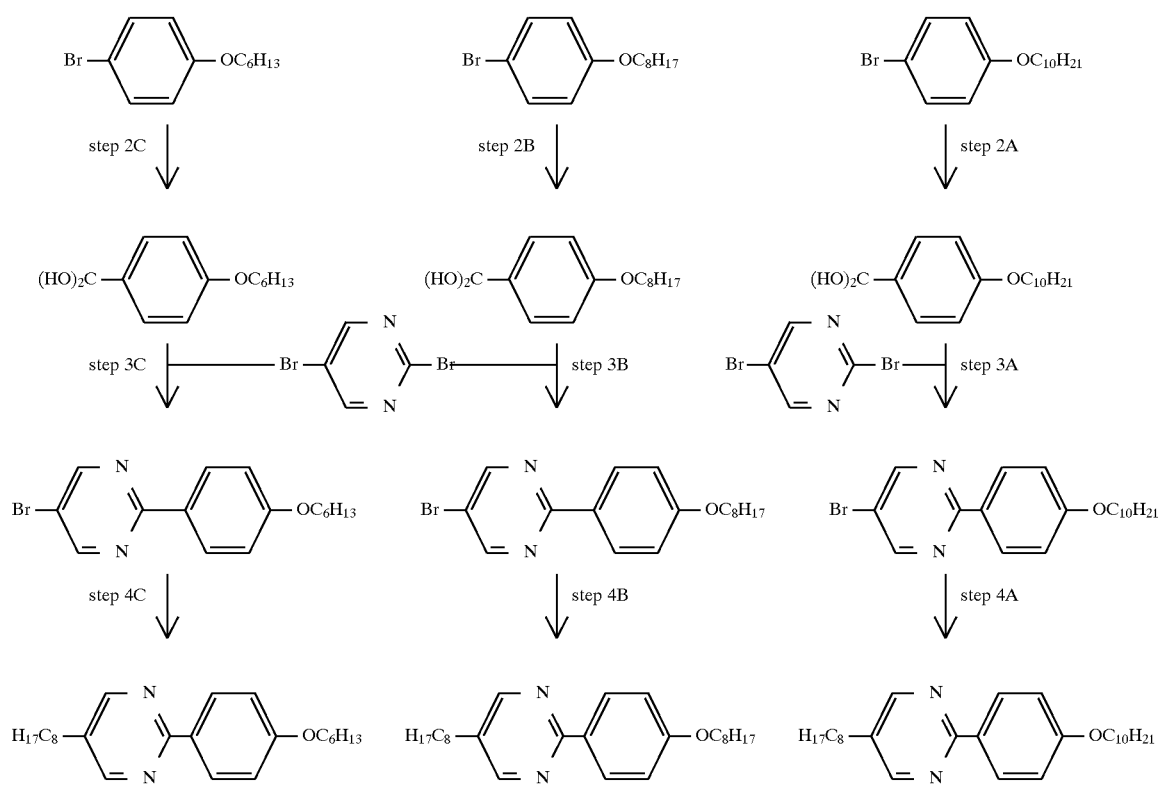
Scheme 2B
8 Synthetic steps
step 1
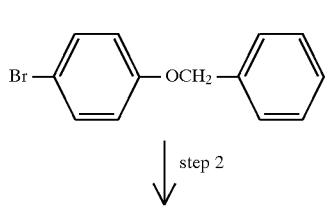
step 2

-continued
Scheme 2B

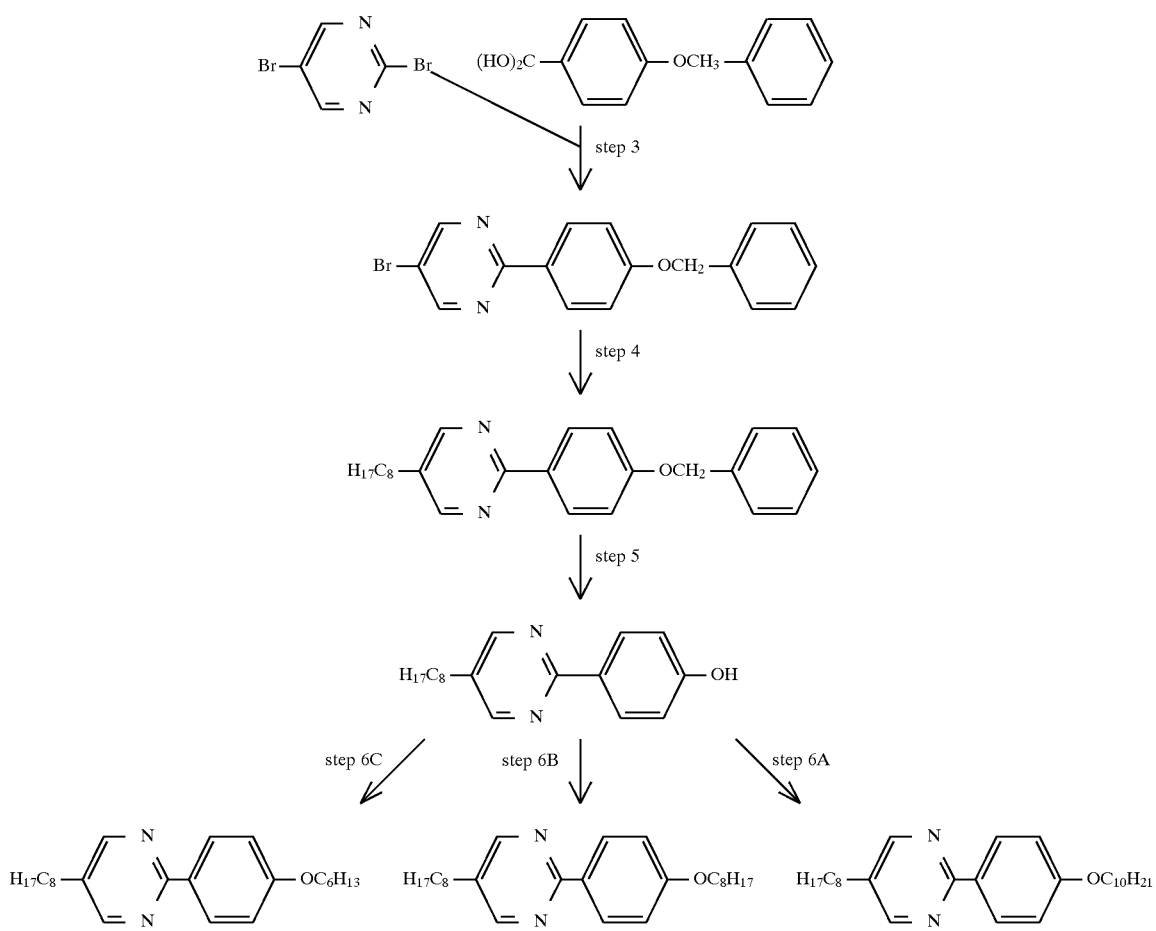

The excellent suitability of the compounds (I) as universal precursors, for example for liquid crystals, is furthermore confirmed by scheme 3. EP-A 508 330 proposes a liquid-crystal compound comprising two types of phenyl pyrimidines, of which each type is represented in the mixture by 3 homologs (Table 4, Example 14):
Type A: 2-(4-alkoxyphenyl)-5-alkylpyrimidines
Type B: 2-(4-alkylbiphenyl)-4'-yl)-5-alkylpyrimidines Scheme 3 shows that the novel compound (Ib) is suitable for the preparation of both types. This enables the preparation of a relatively large amount of (Ib), which is a significant advantage, from the point of view of both process economy and process ecology, compared with the linear synthesis of each of types A and B, which in each case takes place in small production volumes.

Scheme 4 confirms that a mixture which, besides the above phenylpyrimidine of type A, also contains two further types, C: 5-alkoxy-2-[4-substituted phenyl]pyrimidine
D: 5-(4-substituted phenyl)-2-(4-substituted phenyl) pyrimidine and is proposed in EP-A 469 800, Table 2, Example 9, can also be prepared in a favourable manner from the novel compound (Ib).

In their totality, schemes 1 to 4 confirm that the bifunctional precursors of the formula (I) are suitable for the preparation of a wide variety of types of liquid crystal from a single precursor. The preparation of a precursor which is universal in this way and subsequently the end products derived therefrom can be carried out significantly more economically than that of a plurality of individual precursors.

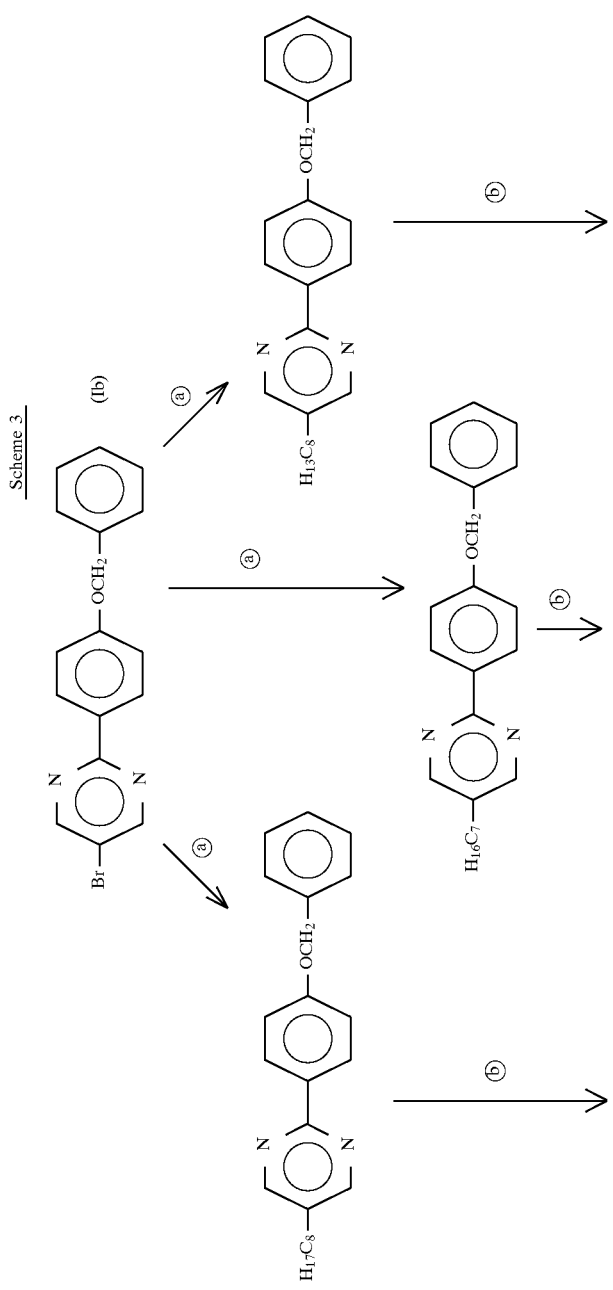

-continued
Scheme 3
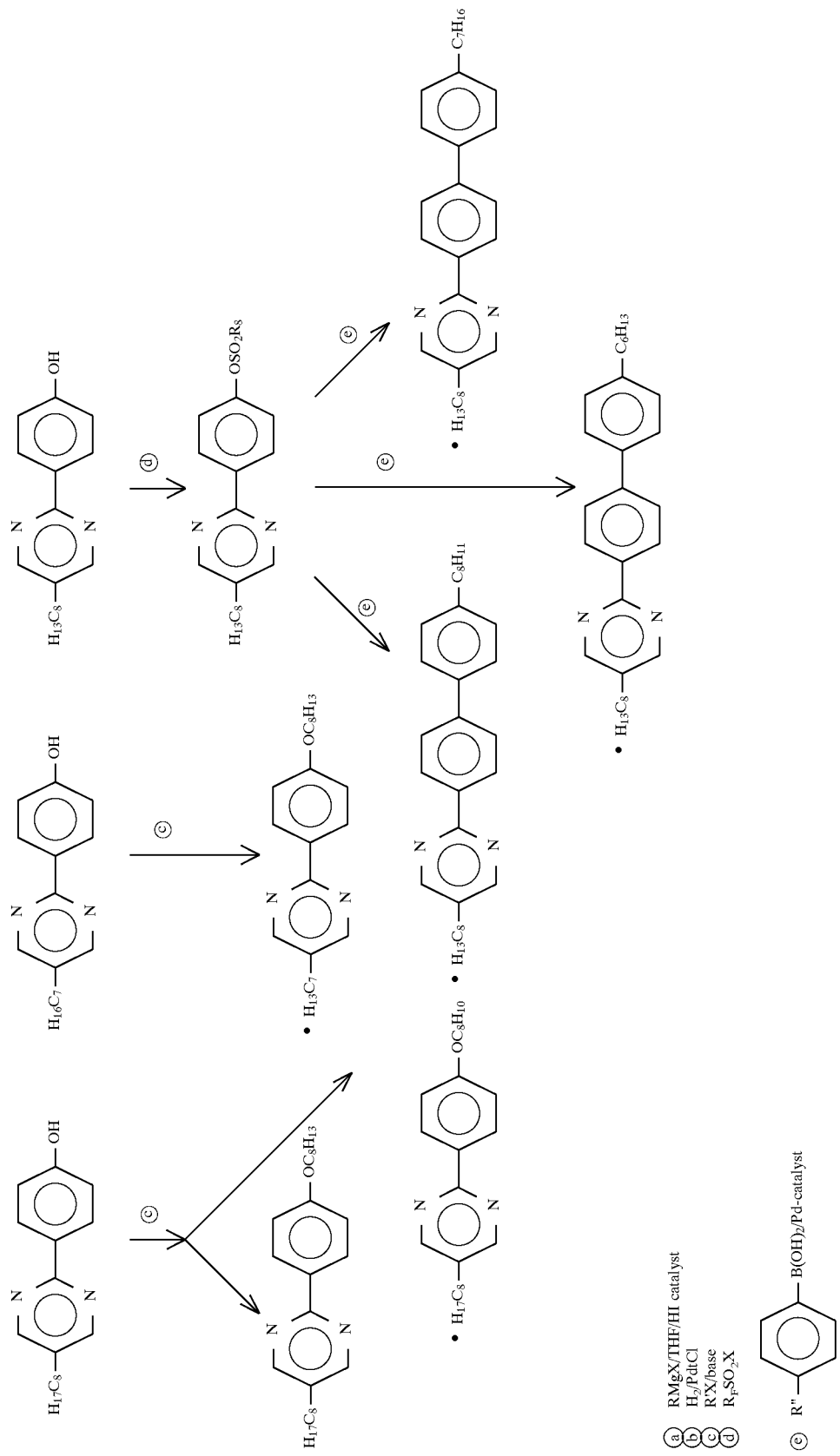

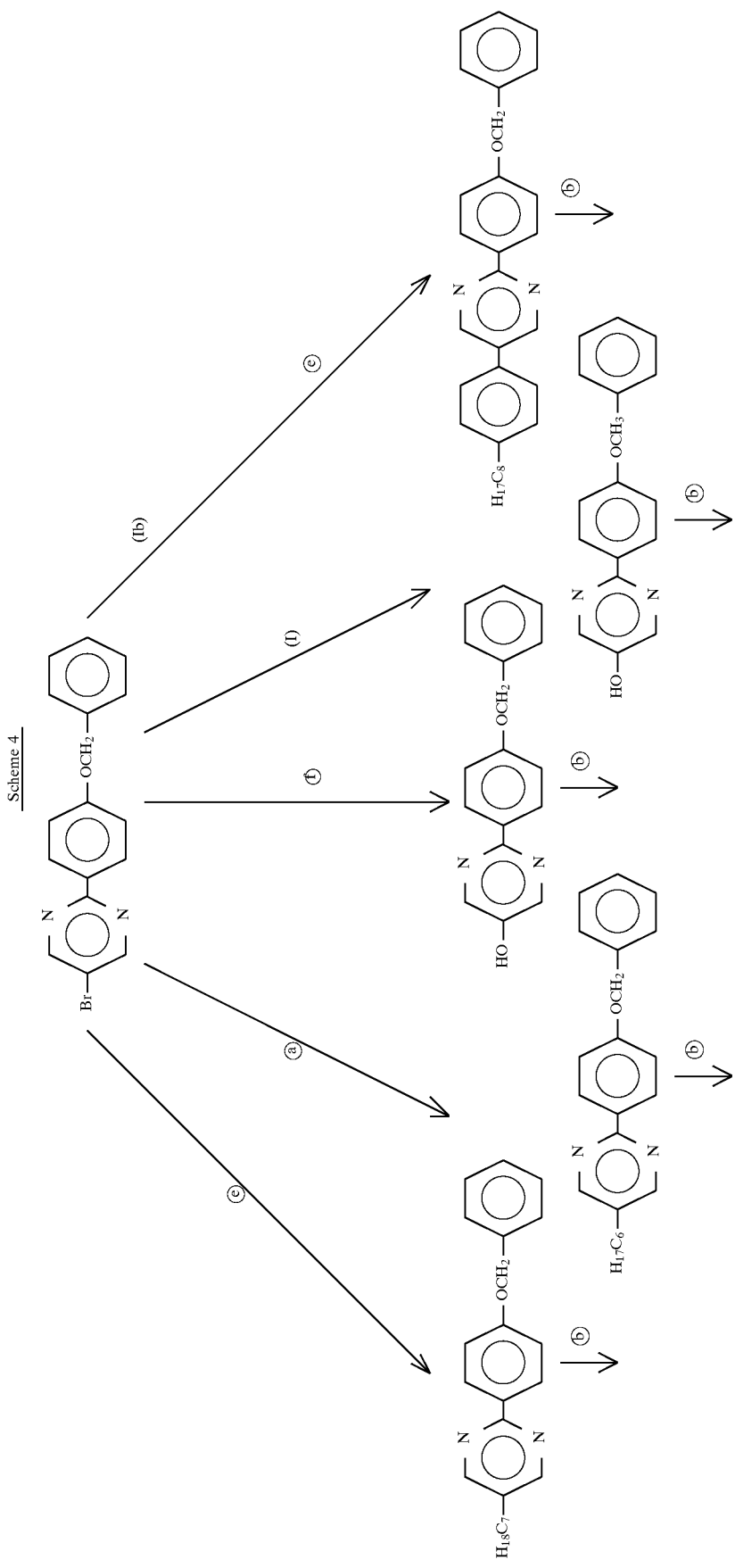

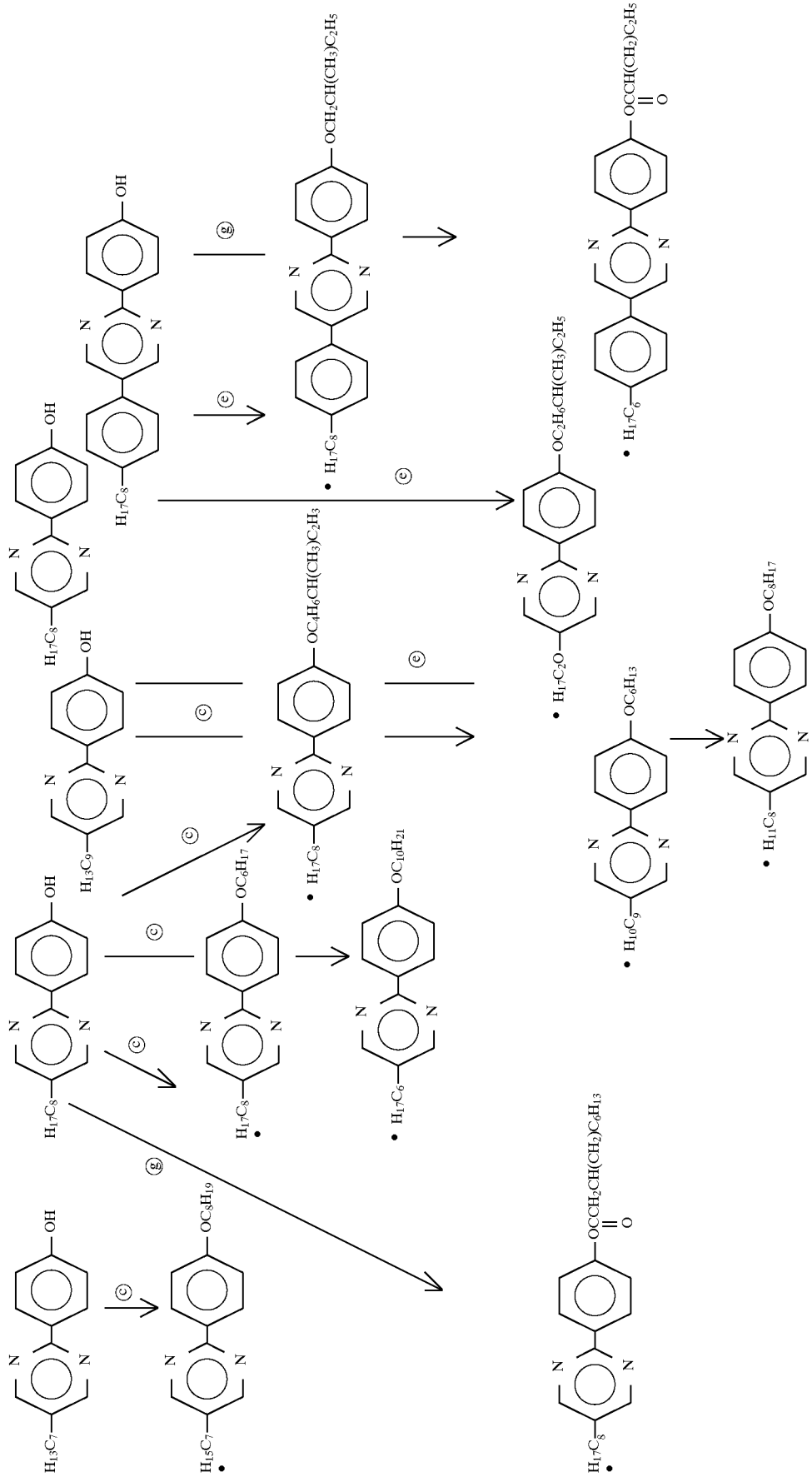

EXAMPLES

Example 1

5-bromo-2-[4-(benzoxy)phenyl]pyrimidine

A solution of 104 g of 2,5-dibromopyrimidine, 100 g of 4-benzoxyphenylboronic acid, 4.75 g of Pd (10% on activated charcoal), 4.5 g of triphenylphosphene and 93 g of sodium carbonate in 1 l of toluene, 0.5 l of ethanol and 0.3 l of water is heated at 80° C. for 24 hours. After filtration, the organic phase is separated off and evaporated to dryness in vacuo. The residue is recrystallized from acetonitrile: 83 g of solids of melting point 153°–155° C.

Examples 2–37 are obtained analogously:

| | |
|---|---|
| Example 2 | 5-bromo-2-[(4-benzoxy-2,3-difluoro)-phenyl]pyrimidine |
| Example 3 | 5-bromo-2-[(4-benzoxy-3-fluoro)phenyl]-pyrimidine |
| Example 4 | 5-bromo-2-[(4-benzoxy-2-fluoro)phenyl]-pyrimidine |
| Example 5 | 5-chloro-2-[(4-benzoxy)phenyl]pyrimidine |
| Example 6 | 5-chloro-2-[4-benzoxy-2,3-difluoro)-phenyl]pyrimidine |
| Example 7 | 5-chloro-2-[(4-benzoxy-3-fluoro)phenyl]-pyrimidine |
| Example 8 | 5-chloro-2-[(4-benzoxy-2-fluoro)phenyl]-pyrimidine |
| Example 9 | 5-iodo-2-[(4-benzoxy)phenyl]pyrimidine |
| Example 10 | 5-iodo-2-[(4-benzoxy-2,3-difluoro)-phenyl]pyrimidine |
| Example 11 | 5-iodo-2-[(4-benzoxy-3-fluoro)phenyl]-pyrimidine |
| Example 12 | 5-iodo-2-[(4-benzoxy-2-fluoro)phenyl]-pyrimidine; |
| Example 13 | deleted |
| Example 14 | 5-bromo-2-[4-benzoxy)phenyl]pyridine; m.p. 159–160° |
| Example 15 | 5-bromo-2-[(4-benzoxy-2,3-difluoro)-phenyl]pyridine |
| Example 16 | 5-bromo-2-[(4-benzoxy-3-fluoro)phenyl]-pyridine |
| Example 17 | 5-bromo-2-[(4-benzoxy-2-fluoro)phenyl]-pyridine |
| Example 18 | 5-chloro-2-[4-benzoxy)phenyl]pyridine |
| Example 19 | 5-chloro-2-[(4-benzoxy-2,3-difluoro)-phenyl]pyridine |
| Example 20 | 5-chloro-2-[(4-benzoxy-3-fluoro)-phenyl]pyridine |
| Example 21 | 5-chloro-2-[(4-benzoxy-2-fluoro)phenyl]-pyridine |
| Example 22 | 5-iodo-2-[(4-benzoxy)phenyl]pyridine |
| Example 23 | 5-iodo-2-[(4-benzoxy-2,3-difluoro)-phenyl]pyridine |
| Example 24 | 5-iodo-2-[(4-benzoxy-3-fluoro)phenyl]-pyridine |
| Example 25 | 5-iodo-2-[(4-benzoxy-2-fluoro)phenyl]-pyridine |
| Example 26 | 5-bromo-2-[4-(benzoxy)phenyl]pyrazine |
| Example 27 | 5-bromo-2-[(4-benzoxy-2,3-difluoro)-phenyl]pyrazine |
| Example 28 | 5-bromo-2-[(4-benzoxy-3-fluoro)phenyl]-pyrazine |
| Example 29 | 5-bromo-2-[(4-benzoxy-2-fluoro)phenyl]-pyrazine |
| Example 30 | 5-chloro-2-[4-(benzoxy)phenyl]pyrazine |
| Example 31 | 5-chloro-2-[(4-benzoxy-2,3-difluoro)-phenyl]pyrazine |
| Example 32 | 5-chloro-2-[(4-benzoxy-3-fluoro)phenyl]-pyrazine |
| Example 33 | 5-chloro-2-[(4-benzoxy-2-fluoro)-phenyl]pyrazine |
| Example 34 | 5-iodo-2-[4-(benzoxy)phenyl]pyrazine |
| Example 35 | 5-iodo-2-[4-benzoxy-2,3-difluor)phenyl]-pyrazine |
| Example 36 | 5-iodo-2-[(4-benzoxy-3-fluoro)phenyl]-pyrazine |
| Example 37 | 5-iodo-2-[(4-benzoxy-3-fluoro)phenyl]-pyrazine |
| Example 38 | 5-bromo-2-[5-benzoxypyridin-2-yl]-pyrimidine |
| Example 38 a | 6-bromo-3-(4-benzoxy)phenylpyridazine |
| Example 38 b | 6-chloro-3-(4-benzoxy)phenylpyridazine; m.p. 186–189° C. |
| Example 38 c | 6-iodo-3-(4-benzoxy)phenylpyridazine |

Example 39

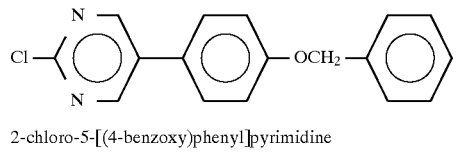

2-chloro-5-[(4-benzoxy)phenyl]pyrimidine

A solution of 3.87 g of 5-bromo-2-chloropyrimidine, 4.56 g of 4-benzoxyphenylphenylboronic acid, 0.24 g of tetrakis (triphenylphosphene)palladium(0) and 4.2 g of sodium carbonate in 45 ml of toluene, 22 ml of ethanol and 15 ml of water is heated at the boil for 2 hours. Work-up as in Example 1 and purification by chromatography (SiO$_2$/CH$_2$Cl$_2$) gives 4.1 g of colorless solid of melting point 158°–160° C.

Examples 40–54 are obtained analogously:

| | |
|---|---|
| Example 40 | 2-chloro-5-[(4-benzoxy-2,3-difluoro)-phenyl]pyrimidine |
| Example 41 | 2-chloro-5-[(4-benzoxy-3-fluoro)phenyl]-pyrimidine |
| Example 42 | 2-chloro-5-[(4-benzoxy-2-fluoro)phenyl]-pyrimidine |
| Example 43 | 2-bromo-5-[(4-benzoxy-2,3-difluoro)-phenyl]pyrimidine |
| Example 44 | 2-bromo-5-[(4-benzoxy-2,3-difluoro)-phenyl]pyrimidine |
| Example 45 | 2-bromo-5-[(4-benzoxy-3-fluoro)phenyl]-pyrimidine |
| Example 46 | 2-bromo-5-[(4-benzoxy-2-fluoro)phenyl]-pyrimidine |
| Example 47 | 2-bromo-5-[(4-benzoxy)phenyl]pyridine |
| Example 48 | 2-bromo-5-[(4-benzoxy-2,3-difluoro)-phenyl]pyridine |
| Example 49 | 2-bromo-5-[(4-benzoxy-3-fluoro)phenyl]-pyridine |
| Example 50 | 2-bromo-5-[(4-benzoxy-2-fluoro)phenyl]-pyridine |
| Example 51 | 2-chloro-5-[(4-benzoxy)phenyl]pyridine |
| Example 52 | 2-chloro-5-[(4-benzoxy-2,3-difluoro)-phenyl]pyridine |
| Example 53 | 2-chloro-5-[(4-benzoxy-3-fluoro)phenyl]-pyridine |
| Example 54 | 2-chloro-5-[(4-benzoxy-2-fluoro)phenyl]-pyridine |

Example 55

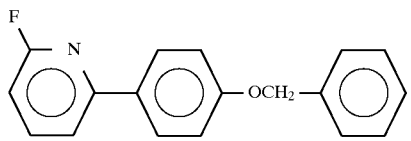

A solution of 17.6 g of 2-bromo-6-fluoropyridine (preparation as described in DE-A 4 040 575), 22.8 g of 4-benzoxyphenylboronic acid and 21.2 g of sodium carbonate in 300 ml of toluene, 150 ml of ethanol and 100 ml of water is refluxed for 2 hours in the presence of tetrakis (triphenylphosphene)palladium (0). The organic phase is separated off and evaporated to dryness in vacuo: 31 g of crude product; recrystallization from 220 ml of acetonitrile gives 20.8 g of product.

Examples 56–58 are obtained analogously:

| | |
|---|---|
| Example 56 | 6-fluoro-3-[(4-benzoxy-2,3-difluoro)-phenyl]pyridine |
| Example 57 | 6-fluoro-2-[(4-benzoxy-3-fluoro)phenyl]-pyridine |
| Example 58 | 6-fluoro-2-[(4-benzoxy-2-fluoro)phenyl]-pyridine |

Example 59

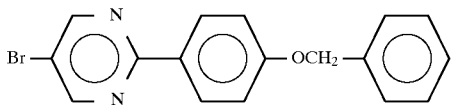

A solution of 37.2 g of 4-bromophenyl trifluoromethanesulfonate, 34.2 g of 4-benzoxyphenylboronic acid, 1.8 g of tetrakis (triphenylphosphene)palladium (0) and 50 g of sodium carbonate in 450 ml of toluene, 225 ml of ethanol and 150 ml of water is refluxed for 12 hours. Work-up as in Example 1 and recrystallization of acetonitrile gives 34.2 g of colorless crystals at melting point 157°–158° C.

Examples 60–127 are obtained analogously:

| | |
|---|---|
| Example 60 | 4-bromo-4'-benzoxy-2',3'-difluorobiphenyl |
| Example 61 | 4-bromo-4'-benzoxy-2'-fluorobiphenyl |
| Example 62 | 4-bromo-4'-benzoxy-3'fluorobiphenyl |
| Example 63 | 4-bromo-3-fluoro-4'-benzoxybiphenyl |
| Example 64 | 4-bromo-3-fluoro-4'-benzoxy-2',3'-difluorobiphenyl |
| Example 65 | 4-bromo-3-fluoro-4'-benzoxy-2'-fluoro-biphenyl |
| Example 66 | 4-bromo-3-fluoro-4'-benzoxy-3'-fluoro-biphenyl |
| Example 67 | 4-bromo-2-fluoro-4'-benzoxybiphenyl |
| Example 68 | 4-bromo-2-fluoro-4'-benzoxy-2',3'-difluorobiphenyl |
| Example 69 | 4-bromo-2-fluoro-4'-benzoxy-2-fluoro-biphenyl |
| Example 70 | 4-bromo-2-fluoro-4'-benzoxy-3'-fluoro-biphenyl |
| Example 71 | 4-bromo-2,3-difluoro-4'-benzoxybiphenyl |
| Example 72 | 4-bromo-2,3-difluoro-4'-benzoxy-2',3'-difluorobiphenyl |
| Example 73 | 4-bromo-2,3-difluoro-4'-benzoxy-2'-fluorobiphenyl |
| Example 74 | 4-bromo-2,3-difluoro-4'-benzoxy-3'-fluorobiphenyl |
| Example 75 | 4-bromo-4"-benzoxy-p-terphenyl |
| Example 76 | 4-bromo-4"-benzoxy-2",3"-difluoro-p-terphenyl |
| Example 77 | 4-bromo-4"-benzoxy-2"-fluoro-p-terphenyl |
| Example 78 | 4-bromo-4"-benzyloxy-3"-fluoro-p-terphenyl |
| Example 79 | 4-bromo-4"-benzoxy-2',3'-difluoro-p-terphenyl |
| Example 80 | 4-bromo-4"-benzoxy-2'-fluoro-p-terphenyl |
| Example 81 | 4-bromo-4"-benzoxy-3'-fluoro-p-terphenyl |
| Example 82 | 4-bromo-3-fluoro-4"-benzoxy-p-terphenyl |
| Example 83 | 4-bromo-3-fluoro-4"-benzoxy-2",3"-difluoro-p-terphenyl |
| Example 84 | 4-bromo-3-fluoro-4"-benzoxy-2',3'-difluoro-p-terphenyl |
| Example 85 | 4-bromo-3-fluoro-4"-benzoxy-2',2",3',3"-tetrafluoro-p-terphenyl |
| Example 86 | 4-bromo-3-fluoro-4"-benzoxy-2',2",3'-trifluoro-p-terphenyl |
| Example 87 | 4-bromo-3-fluoro-4"-benzoxy-2',2",3"-trifluoro-p-terphenyl |
| Example 88 | 4-bromo-3-fluoro-4"-benzoxy-2',2"-difluoro-p-terphenyl |
| Example 89 | 4-bromo-3-fluoro-4"-benzoxy-2',3"-difluoro-p-terphenyl |
| Example 90 | 4-bromo-3-fluoro-4"-benzoxy-3',3"-difluoro-p-terphenyl |
| Example 91 | 4-bromo-3-fluoro-4"-benzoxy-3',2"-difluoro-p-terphenyl |
| Example 92 | 4-bromo-3-fluoro-4"-benzoxy-2'-fluoro-p-terphenyl |
| Example 93 | 4-bromo-3-fluoro-4"-benzoxy-3'-fluoro-p-terphenyl |
| Example 94 | 4-bromo-3-fluoro-4"-benzoxy-2"-fluoro-p-terphenyl |
| Example 95 | 4-bromo-3-fluoro-4"-benzoxy-3"-fluoro-p-terphenyl |
| Example 96 | 4-bromo-2-fluoro-4"-benzoxy-p-terphenyl |
| Example 97 | 4-bromo-2-fluoro-4"-benzoxy-2",3"-difluoro-p-terphenyl |
| Example 98 | 4-bromo-2-fluoro-4"-benzoxy-2',3'-difluoro-p-terphenyl |
| Example 99 | 4-bromo-2-fluoro-4"-benzoxy-2',2",3',3"-tetrafluoro-p-terphenyl |
| Example 100 | 4-bromo-2-fluoro-4"-benzoxy-2',2",3'-trifluoro-p-terphenyl |
| Example 101 | 4-bromo-2-fluoro-4"-benzoxy-2',2",3"-trifluoro-p-terphenyl |
| Example 102 | 4-bromo-2-fluoro-4"-benzoxy-2',2"-difluoro-p-terphenyl |
| Example 103 | 4-bromo-2-fluoro-4"-benzoxy-2',3"-difluoro-p-terphenyl |
| Example 104 | 4-bromo-2-fluoro-4"-benzoxy-3',3"-difluoro-p-terphenyl |
| Example 105 | 4-bromo-2-fluoro-4"-benzoxy-3',2"-difluoro-p-terphenyl |
| Example 106 | 4-bromo-2-fluoro-4"-benzoxy-2"-fluoro-p-terphenyl |
| Example 107 | 4-bromo-2-fluoro-4"-benzoxy-3'-fluoro-p-terphenyl |
| Example 108 | 4-bromo-2-fluoro-4"-benzoxy-2"-fluoro-p-terphenyl |
| Example 109 | 4-bromo-2-fluoro-4"-benzoxy-3"-fluoro-p-terphenyl |
| Example 110 | 4-bromo-2,3-difluoro-4"-benzoxy-p-terphenyl |
| Example 111 | 4-bromo-2,3-difluoro-4"-benzoxy-2",3"-difluoro-p-terphenyl |
| Example 112 | 4-bromo-2,3-difluoro-4"-benzoxy-2',3'-difluoro-p-terphenyl |
| Example 113 | 4-bromo-2,3-difluoro-4"-benzoxy-2',2",3',3"-tetrafluoro-p-terphenyl |
| Example 114 | 4-bromo-2,3-difluoro-4"-benzoxy-2',2",3'-trifluoro-p-terphenyl |
| Example 115 | 4-bromo-2,3-difluoro-4"-benzoxy-2',2",3"-trifluoro-p-terphenyl |
| Example 116 | 4-bromo-2,3-difluoro-4"-benzoxy-2',2"-difluoro-p-terphenyl |
| Example 117 | 4-bromo-2,3-difluoro-4"-benzoxy-2',3"- |

| | |
|---|---|
| Example 118 | difluoro-p-terphenyl |
| | 4-bromo-2,3-difluoro-4"-benzoxy-3',3"-difluoro-p-terphenyl |
| Example 119 | 4-bromo-2,3-difluoro-4"-benzoxy-3',2"-difluoro-p-terphenyl |
| Example 120 | 4-bromo-2,3-difluoro-4"-benzoxy-2'-fluoro-p-terphenyl |
| Example 121 | 4-bromo-2,3-difluoro-4"-benzoxy-3'-fluoro-p-terphenyl |
| Example 122 | 4-bromo-2,3-difluoro-4"-benzoxy-2"-fluoro-p-terphenyl |
| Example 123 | 4-bromo-2,3-difluoro-4"-benzoxy-3"-fluoro-p-terphenyl |
| Example 124 | 6-bromo-2-(4-benzoxy)phenyl-naphthalene |
| Example 125 | 6-bromo-2-(4-benzoxy-2,3-difluoro)phenyl-naphthalene |
| Example 126 | 6-bromo-2-(4-benzoxy-2-fluoro)phenyl-naphthalene |
| Example 127 | 6-bromo-2-(4-benzoxy-3-fluoro)phenyl-naphthalene |

Example 128

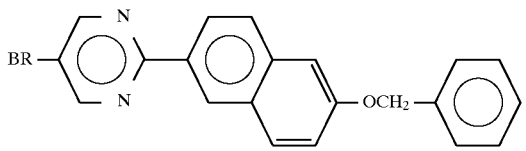

is obtained analogously to Example 1 by coupling of 2,5-dibromopyrimidine and 6-benzoxynaphthalene-2-boronic acid.

Examples 129–131 are obtained analogously:

| | |
|---|---|
| Example 129 | 5-bromo-2-[6-benzoxynapthalene-2-yl]pyridine |
| Example 130 | 2-bromo-5-[6-benzoxynapthalene-2-yl]pyridine |
| Example 131 | 2-bromo-5-[6-benzoxynapthalene-2-yl]-pyridine |

Example 132

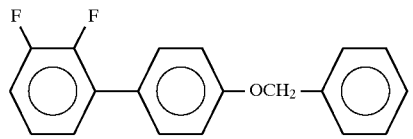

is obtained analogously to Example 59 by coupling of 2,3-difluorophenylboronic acid and 4-benzoxybromobenzene; as colorless crystals of melting point 82°–83° C.

Examples 133–169 are obtained analogously:

| | |
|---|---|
| Example 133 | 3-fluoro-4'-benzoxybiphenyl |
| Example 134 | 3-fluoro-4'-benzoxy-2',3'-difluorobiphenyl |
| Example 135 | 3-fluoro-4'-benzoxy-2'-fluorobiphenyl |
| Example 136 | 3-fluoro-4'-benzoxy-3'-fluorobiphenyl |
| Example 137 | 2,3-difluoro-4'-benzoxybiphenyl |
| Example 138 | 2,3-difluoro-4'-benzoxy-2',3'-difluoro-biphenyl |
| Example 139 | 2,3-difluoro-4'-benzoxy-2'-fluorobiphenyl |
| Example 140 | 2,3-difluoro-4'-benzoxy-3'-fluorobiphenyl |
| Example 141 | deleted |
| Example 142 | 3-fluoro-4"-benzoxy-p-terphenyl |
| Example 143 | 3-fluoro-4"-benzoxy-2",3"-difluoro-p-terphenyl |
| Example 144 | 3-fluoro-4"-benzoxy-2',3'-difluoro-p-terphenyl |
| Example 145 | 3-fluoro-4"-benzoxy-2',2",3',3"-tetrafluoro-p-terphenyl |
| Example 146 | 3-fluoro-4"-benzoxy-2',2",3'-trifluoro-p-terphenyl |
| Example 147 | 3-fluoro-4"-benzoxy-2',2",3"-trifluoro-p-terphenyl |
| Example 148 | 3-fluoro-4"-benzoxy-2',2"-difluoro-p-terphenyl |
| Example 149 | 3-fluoro-4"-benzoxy-2',3"-difluoro-p-terphenyl |
| Example 150 | 3-fluoro-4"-benzoxy-3',3"-difluoro-p-terphenyl |
| Example 151 | 3-fluoro-4"-benzoxy-3',2"-difluoro-p-terphenyl |
| Example 152 | 3-fluoro-4"-benzoxy-2'-fluoro-p-terphenyl |
| Example 153 | 3-fluoro-4"-benzoxy-3'-fluoro-p-terphenyl |
| Example 154 | 3-fluoro-4"-benzoxy-2"-fluoro-p-terphenyl |
| Example 155 | 3-fluoro-4"-benzoxy-3"-fluoro-p-terphenyl |
| Example 156 | 2,3-difluoro-4"-benzoxy-p-terphenyl |
| Example 157 | 2,3-difluoro-4"-benzoxy-2",3"-difluoro-p-terphenyl |
| Example 158 | 2,3-difluoro-4"-benzoxy-2',3'-difluoro-p-terphenyl |
| Example 159 | 2,3-difluoro-4"-benzoxy-2',2",3',3"-tetrafluoro-p-terphenyl |
| Example 160 | 2,3-difluoro-4"-benzoxy-2',2",3'-trifluoro-p-terphenyl |
| Example 161 | 2,3-difluoro-4"-benzoxy-2',2",3"-trifluoro-p-terphenyl |
| Example 162 | 2,3-difluoro-4"-benzoxy-2',2"-difluoro-p-terphenyl |
| Example 163 | 2,3-difluoro-4"-benzoxy-2',3"-difluoro-p-terphenyl |
| Example 164 | 2,3-difluoro-4"-benzoxy-3',3"-difluoro-p-terphenyl |
| Example 165 | 2,3-difluoro-4"-benzoxy-3',2"-difluoro-p-terphenyl |
| Example 166 | 2,3-difluoro-4"-benzoxy-2'-fluoro-p-terphenyl |
| Example 167 | 2,3-difluoro-4"-benzoxy-3'-fluoro-p-terphenyl |
| Example 168 | 2,3-difluoro-4"-benzoxy-2"-fluoro-p-terphenyl |
| Example 169 | 2,3-difluoro-4"-benzoxy-3"-fluoro-p-terphenyl |

We claim:

1. A bifunctional compound of the formula (I),

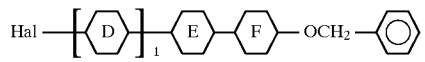

(I)

in which:

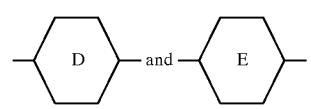

are naphthalene-2,6-diyl or

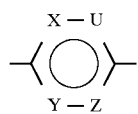

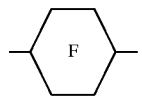

is naphthalene-2,6-diyl or

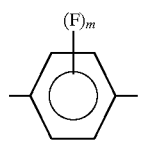

U, X, Y and Z are —CH═, —CF═ and —N═, with the proviso that —CF═ and —N═ may each only be represented at most twice per six-membered ring, and that —CF═ and —N═ may not at the same time be represented twice in a six-membered ring;
Hal is Cl, Br or I; or H, if X and/or Y are —CF═
l is 0 or 1
m is 0, 1, 2 or 3.

2. A bifunctional compound as claimed in claim 1, where the symbols in the formula I have the following meanings:
l═0
at least one of U, X, Y and Z is —N═ and at most one is —CF═, and the others are —CH═
m is 0, 1 or 2
n is 0, 1 or 2
Hal is Br or I.

3. A bifunctional compound as claimed in claim 1 or 2, where the symbols in the formula I have the following meanings:
l═0
one or two of U, X, Y and Z is —N═, and the others are —CH═
m is 0, 1, 2 or 3
Hal is Br or I.

4. An intermediate for the preparation of components of liquid-mixtures, of the formula (VI)

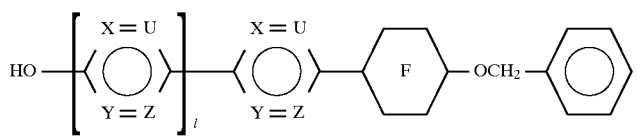

where the symbols are as defined in the formula (I) in claim 1 and, for the ring carrying the OH function, U and/or Z must be —N═, but X and/or Y must not be —N═.

5. A process for the preparation of a bifunctional compound of formula (I)

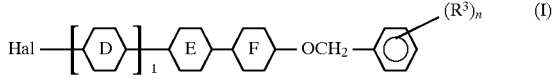

in which:

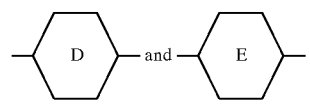

are naphthalene-2,6-diyl or

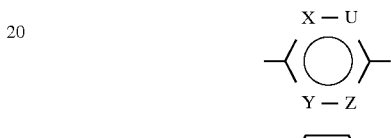

is naphthalene-2,6-diyl or

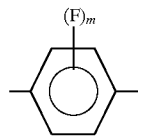

U, X, Y and Z are —CH═, —CF═ and —N═, with the proviso that —CF═ and —N═ may each only be represented at most twice per six-membered ring, and that —CF═ and —N═ may not at the same time be represented twice in a six-membered ring;
Hal is Cl, Br or I; or H, if X and/or Y are —CF═
$R^3$ is $CH_3$ or $OCH_3$
l is 0 or 1
m and n are 0, 1, 2 or 3,
which comprises coupling an arylboronic acid of the formula (XXI)

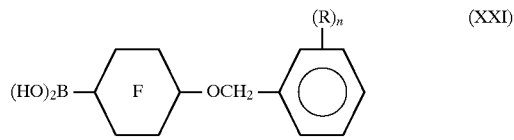

in which the substituents and indices have the following meanings:

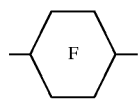

is naphthalene-2,6-diyl or

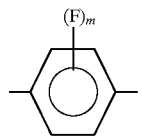

R is CH₃ or OCH₃
m is 0, 1, 2 or 3
n is 0, 1 or 2,
with a halogen compound of the formula (XXII)

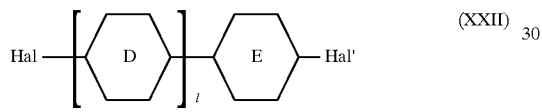

in which
Hal is Cl, Br or I and
Hal' is Cl, Br, I or perfluoroalkanesulfonate, with catalysis by palladium or a palladium compound, to give a compound of the formula I.

6. An intermediate for the preparation of components of liquid-crystal mixtures, of the formula (VII)

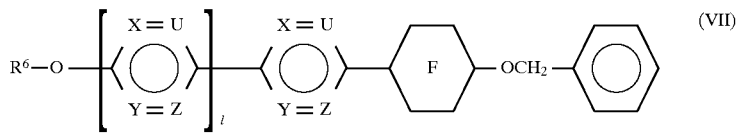

in which

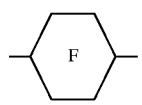

is naphthalene-2,6-diyl or

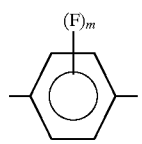

X, Y, U and Z are —CH=, —CF= and —N=, with the proviso that —CH= and —N= may each only be represented at most twice per six-membered ring, and that —CF= and —N= may not at the same time be represented twice in a six-membered ring and that at least one nitrogen atom must be present in the ring bonded to R⁶—O—, and that X and/or Y must not be N in this ring, R⁶ is alkyl having 1 to 18 carbon atoms, in which, in addition, one or more non-adjacent —CH₂— groups can be replaced by —O—, —CH=CH— or —Si(CH₃)₂—,
l is 0 or 1
m is 0, 1, 2, or 3.

7. An intermediate for the preparation of components of liquid-crystal mixtures, of the formula (VIII)

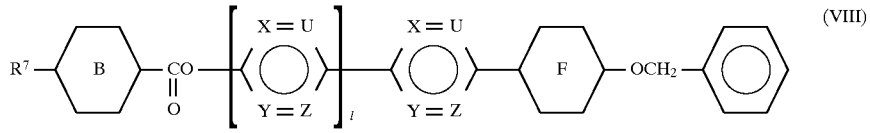

in which

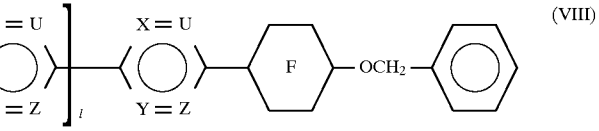

are naphthalene-2,6-diyl or

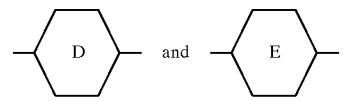

is naphthalene-2,6-diyl or

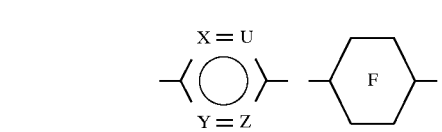

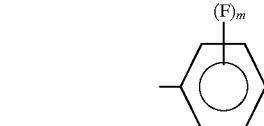 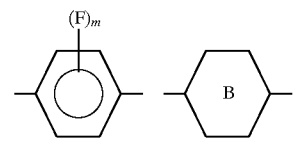

1,4-phenylene, optionally substituted once or twice by F, or is 1,4-cyclohexylene or 1,3-dioxane-2,5-diyl;

U, X, Y and Z are —CH=, —CF= and —N=, with the proviso that —CF= and —N= may each only be represented at most twice per six-membered ring, and that —CF= and —N= may not at the same time be represented twice in a six-membered ring;

R⁷ is alkyl having 1 to 18 carbon atoms, in which, in addition, one or more non-adjacent —CH₂— groups can be replaced by —O—, —CH=CH— or —Si (CH₃)—,
l is 0 or 1
m is 0, 1, 2 or 3.

8. An intermediate for the preparation of components of liquid-crystal mixtures, of the formula (XIII),

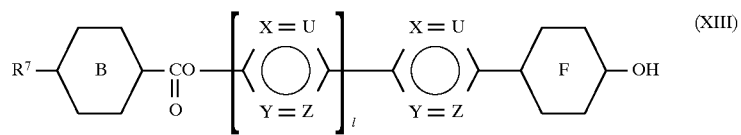
in which the symbols are as defined in the formula (VIII) in claim 1.
* * * * *